US010908080B2

(12) United States Patent
Salazar et al.

(10) Patent No.: US 10,908,080 B2
(45) Date of Patent: Feb. 2, 2021

(54) FIELD DEPLOYABLE SOIL OBSERVATION TOPOGRAPHIC DIFFERENTIAL ABSORPTION LIDAR (SOTDIAL)

(71) Applicant: BOARD OF TRUSTEES OF THE UNIVERSITY OF ARKANSAS, Fayetteville, AR (US)

(72) Inventors: Sean E. Salazar, Fayetteville, AR (US); Richard A. Coffman, Fayetteville, AR (US); Cyrus D. Garner, Lexington, KY (US)

(73) Assignee: Board Of Trustees Of The University Of Arkansas, Fayetteville, AR (US)

( * ) Notice: Subject to any disclaimer, the term of this patent is extended or adjusted under 35 U.S.C. 154(b) by 0 days.

(21) Appl. No.: 16/559,535

(22) Filed: Sep. 3, 2019

(65) Prior Publication Data

US 2020/0018695 A1    Jan. 16, 2020

Related U.S. Application Data

(63) Continuation of application No. 15/671,040, filed on Aug. 7, 2017, now abandoned.

(60) Provisional application No. 62/371,288, filed on Aug. 5, 2016.

(51) Int. Cl.
| | |
|---|---|
| *G01N 21/3554* | (2014.01) |
| *G01S 17/88* | (2006.01) |
| *G01N 21/359* | (2014.01) |
| *G01N 33/24* | (2006.01) |
| *G01N 21/17* | (2006.01) |

(52) U.S. Cl.
CPC ....... *G01N 21/3554* (2013.01); *G01N 21/359* (2013.01); *G01N 33/246* (2013.01); *G01S 17/88* (2013.01); *G01N 2021/1797* (2013.01); *G01N 2201/0612* (2013.01)

(58) Field of Classification Search
None
See application file for complete search history.

(56) References Cited

U.S. PATENT DOCUMENTS

| | | | |
|---|---|---|---|
| 9,585,307 B2 * | 3/2017 | Holland | G01N 21/31 |
| 2012/0060588 A1 | 3/2012 | Ng | |
| 2015/0014543 A1 | 1/2015 | Weidmann | |
| 2015/0277440 A1 | 10/2015 | Kimchi | |
| 2016/0223766 A1 * | 8/2016 | White | H01S 3/0071 |
| 2016/0356890 A1 | 12/2016 | Fried | |
| 2017/0146639 A1 | 5/2017 | Carothers | |
| 2017/0223747 A1 | 8/2017 | Gall | |

OTHER PUBLICATIONS

Kwast, "Quantification of top soil moisture patterns, Evaluation of field methods, process-based modelling, remote sensing and an integrated approach" Netherlands Geographical Studies 381, 2009, p. 1-311. (Year: 2009).*

(Continued)

*Primary Examiner* — David P Porta
*Assistant Examiner* — Mamadou Faye
(74) *Attorney, Agent, or Firm* — Keith A. Vogt; Keith A. Vogt, Ltd

(57) ABSTRACT

A soil analysis system that provides a field deployable device that is configured to remotely measure in situ soil suction through correlation with relative humidity at the soil surface.

20 Claims, 9 Drawing Sheets

(56) References Cited

OTHER PUBLICATIONS

Grant, W.B, 1982, "Effect of differential spectral reflectance on DIAL measurements using topographic targets," Applied Optics, vol. 21, No. 13, pp. 2390-2394.
Hardesty, R.M., 1984, Coherent DIAL measurement of range-resolved water vapor concentration: Applied Optics, vol. 23, No. 15, pp. 2545-2553.
Machol, J.L, et al; 2004, "Preliminary measurements with an automated compact differential absorption lidar for the profiling of water vapor", Applied Optics, vol. 43, No. 5, pp. 3110-3121.
Pierottet et al; 2008; "Linear FMCW laser radar for precision range and vector velocity measurements," Proceedings Material Research Society, San Francisco, CA; Mar. 14018, 2008; 9 pgs.
Nehrir et al; 2009; "Water vapor profiling using a widely tunable, amplified diode-laser-based differential absorption lidar (DIAL)", Journal of Atmospheric and Oceanic Technology, vol. 26, No. 4, pp. 733-745, doI:10.1175/2008JTECHA1201.1.
Adany et al; 2009; Chirped lidar using simplified homodyne detection, Journal of Lightwave Technology, vol. 27, No. 16; pp. 3351-3357.
Spuler et al; 2015; "Field-deployable diode-laser-based differential absorption lidar (DIAL) for profiling water vapor," Atmospheric Measurement Techniques, vol. 8, pp. 1073-1087, doi:10.5194/amt-8-1073-2015.

\* cited by examiner

FIELD DEPLOYABLE SOIL OBSERVATION TOPOGRAPHIC DIFFERENTIAL ABSORPTION LIDAR (SOTDIAL)

RELATED APPLICATIONS

This application is a continuation of U.S. Ser. No. 15/671,040 filed on Aug. 7, 2017 which claims the benefit of U.S. Provisional Application No. 62/371,288 filed Aug. 5, 2016, both of which are herein incorporated by reference.

STATEMENT REGARDING FEDERALLY SPONSORED RESEARCH & DEVELOPMENT

This invention was made with government support under No. OASRTRS-14-H-UARK awarded by the United States Department of Transportation Office of the Assistant Secretary for Research and Technology (U.S. DOT/OST-R) under Research and Innovation Technology Administration (RITA) Cooperative Agreement Award. The government has certain rights in the invention.

INCORPORATION BY REFERENCE OF MATERIAL SUBMITTED ON A COMPACT DISC

Not applicable.

FIELD OF THE INVENTION

Soil suction measurements and soil index properties are important to understanding unsaturated soil mechanics, slope stability, and geo-environmental properties of the soil for its intended use in the field of geotechnical engineering. Current practice requires expensive in situ instrumentation that must be installed and removed by personnel in the field. Furthermore, data collection is sparse (point-wise) and is collected from individually-calibrated devices.

Other current practices require soil samples to be obtained from the field and transported to a laboratory for testing. This practice is time-consuming and costly, while results have been shown to be poorly reproducible.

BRIEF SUMMARY OF THE INVENTION

In certain embodiments, the present invention provides improved characterization of in situ conditions of soil in applications such as embankment slopes, open pit mines, or wildfire basins. The embodiments of the present invention have applicability in the fields of remote sensing, electrical engineering, civil engineering, geotechnical engineering, and geo-environmental engineering.

In another embodiment, the present invention provides a field deployable SOTDiAL device that is configured to remotely measure in situ soil suction through correlation with relative humidity at the soil surface.

In another embodiment, the present invention provides a device that is configured to remotely measure important index properties of the soil that are utilized in classification of the soil, including plasticity and fines content of the soil.

In other embodiments, the present invention provides a SOTDiAL device will significantly advance the field by allowing for remote measurements of soil condition and soil properties.

In other embodiments, the present invention provides a device that reduces the time and costs associated with traditional laboratory classification of soil properties.

In yet other embodiments, the present invention provides a field deployable Soil Observation Topographic Differential Absorption LiDAR (SOTDiAL). The device is a compact remote sensing system that is utilized to determine soil properties remotely.

In yet other embodiments, the present invention provides a SOTDiAL system that is able to remotely-sense soil properties. Direct active and passive measurements made with the system are correlated with in situ soil suction (soil water potential) and index properties used to classify the soil (clay content, plasticity index).

In yet other embodiments, the present invention provides a SOTDiAL system that is easily transportable to any site of interest and the occupation of a single point may provide 360-degree data with unsurpassed spatial and temporal resolution at a range of up to 1500 feet. 360-degrees of data collection may be obtained by configuring the light emitting device and optical aperture to be motorized In yet other embodiments, the present invention provides a SOTDiAL system that may be deployed to scan earthen dams and embankments, mine tailings, landfill liners, unstable slopes, post-wildfire burn basins, or any project where the soil properties may be of interest.

In yet other embodiments, the present invention provides a system that eliminates the need for the installation of expensive instrumentation networks or laboratory testing. Furthermore, the remote measurements may reduce the risk for sites that may be difficult to access or are hazardous to personnel.

In yet other embodiments, the present invention provides a soil analysis system that provides an optical remote sensing instrument having a data acquisition system and a tripod-based telescope which acts as the optical aperture of the system).

In yet other embodiments, the present invention provides a system wherein the data acquisition system consists of an active element where light energy is both transmitted and received by the system and a passive element where light energy is received by the device. In other embodiments, external light is used by the passive element.

In yet other embodiments, the present invention provides a system wherein active light energy is transmitted by two low-power cavity diode lasers arranged in a self-chirped homodyne laser detection scheme tuned to wavelengths of 823.3-nm and 847.0-nm. In other embodiments, the wavelengths used by the active element correspond with water absorption and reflection characteristics. In other embodiments, the wavelengths used by the passive element receive light range from the visual to the near-infrared spectrum (400-nm to 2500-nm).

In other embodiments, the active and passive elements of the system operate in tandem.

In other embodiments, laser light is emitted onto the surface of the soil, while the light is also received simultaneously into the instrument through the optical aperture.

In other embodiments, laser light is partially scattered into the atmosphere, but some light energy is reflected back into the aperture of the system, while the system is adapted to use the remaining backscatter of sun light into the system.

In other embodiments, the present invention provides a system that analyzes the spectra of transmitted and received light and performs a correlation with relative humidity at the soil surface to determine in situ properties of the soil, including soil water potential (i.e. soil suction) and other important index properties of the soil that are utilized in classification of the soil, including plasticity and fines content of the soil.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

DETAILED DESCRIPTION OF THE INVENTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure or system. Further, the terms and phrases used herein are not intended to be limiting, but rather to provide an understandable description of the invention.

Figure 1:
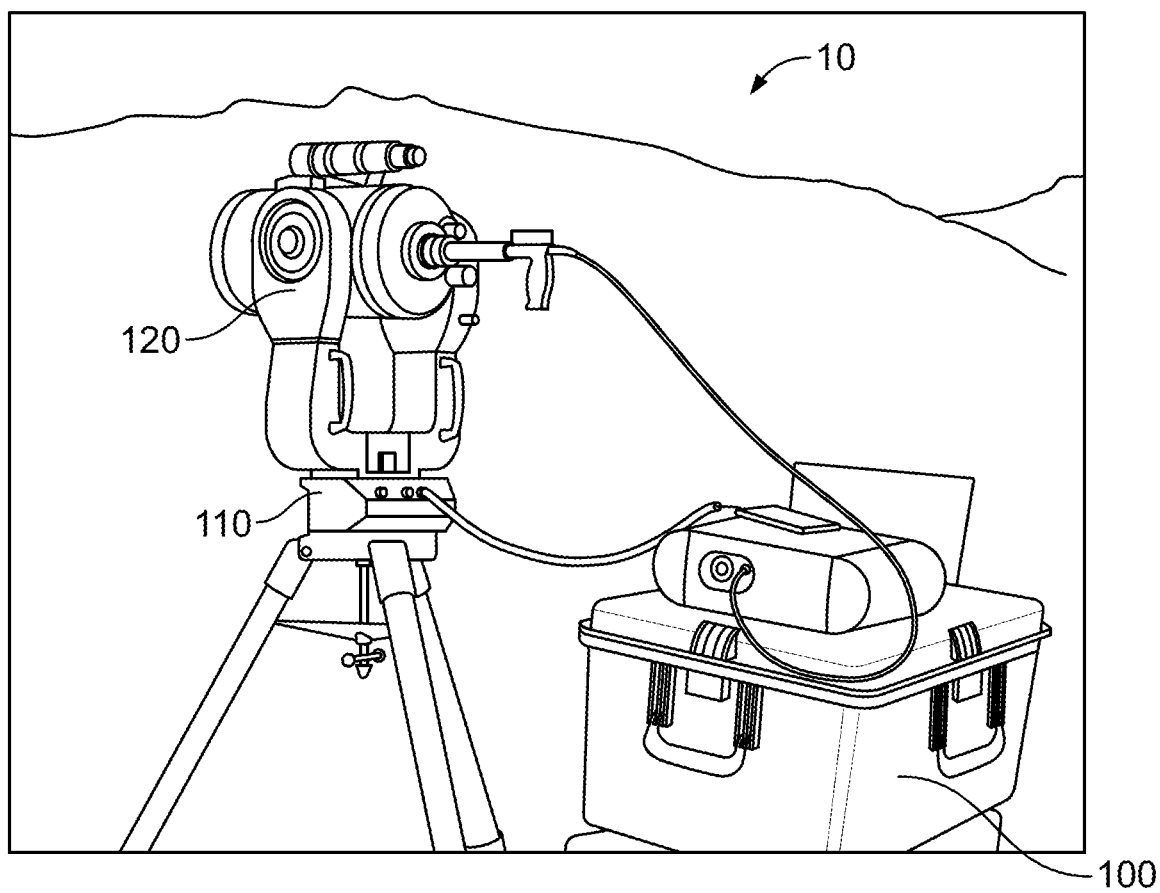
FIG. 1 illustrates a field deployable SOTDiAL device of an embodiment of the present invention.

As shown in FIG. 1, the present invention provides a field deployable SOTDiAL system 10 that is an optical remote sensing instrument. In one preferred embodiment, system 10 includes a 2.5-ft. by 2.5-ft. by 2.5-ft. field box 100 (which contains the heart of the system as well as the data acquisition system), light emitting device 110 and optical aperture 120, which may be a tripod-based telescope. Light emitting device 110 and aperture 120 are active, meaning that light energy is both transmitted and received by the device. In other aspects of the present invention, optical aperture 120 may be a tripod-based telescope.

In a preferred embodiment, active light energy may be transmitted by two low-power cavity diode lasers arranged in a self-chirped homodyne laser detection scheme tuned to wavelengths of 823.3-nm and 847.0-nm. These wavelengths correspond with water absorption and reflection characteristics.

The second element of the device is passive, meaning that the light energy is only received by the device (where the sun is the source of light energy). For the passive portion of the device, the wavelengths of received light range from the visual to the near-infrared spectrum (400-nm to 2500-nm).

In yet other embodiments, light emitting device 110 and aperture 120 may be motorized. Configuring system 10 in this manner allows for the scanning of areas of interest such as earthen dams and embankments, mine tailings, landfill liners, unstable slopes, post-wildfire burn basins, or any other area where the soil properties may be of interest.

Figure 2A:
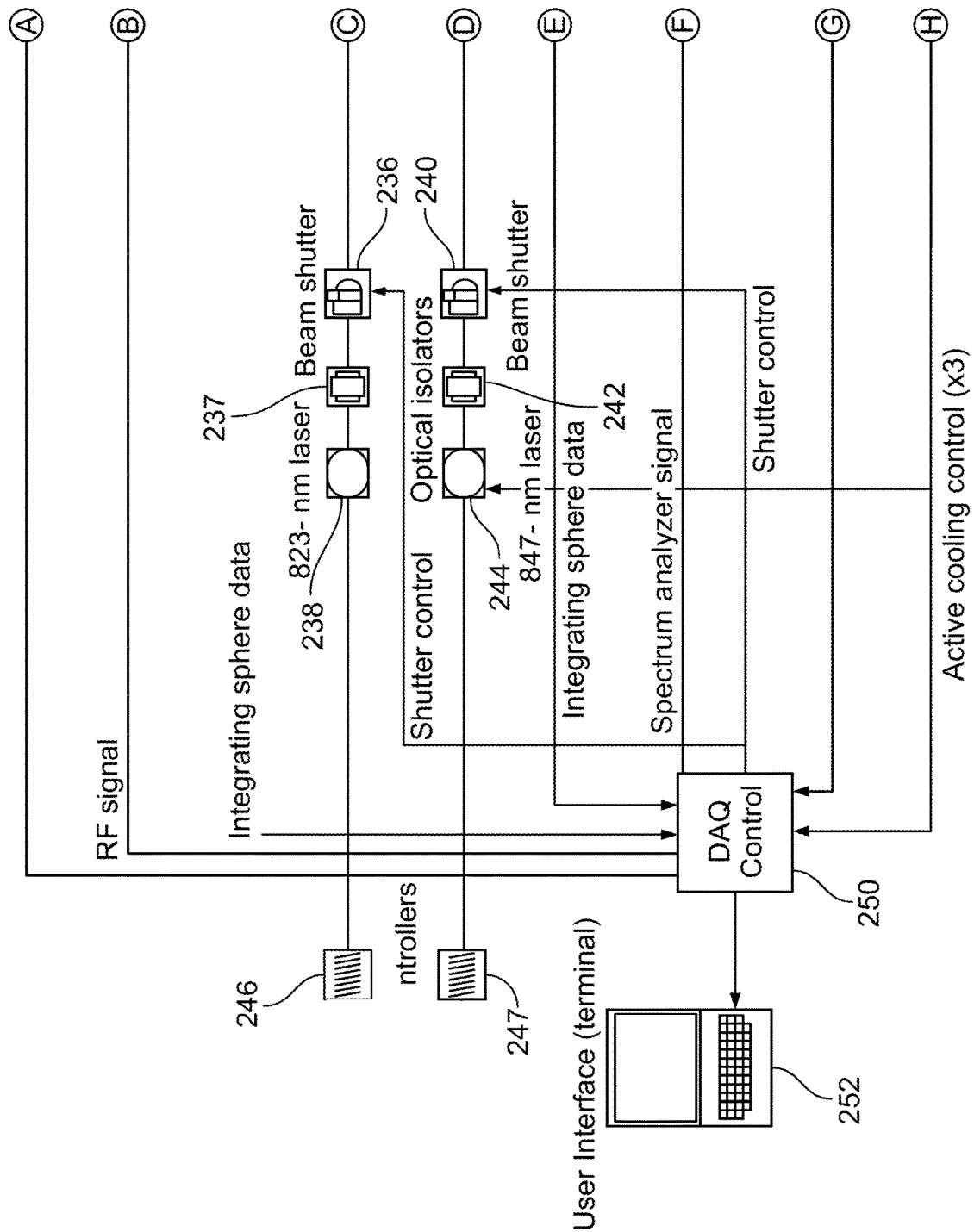
FIGS. 2A and 2B are schematics of the individual components of the SOTDiAL device of an embodiment of the present invention.
Figure 2B:
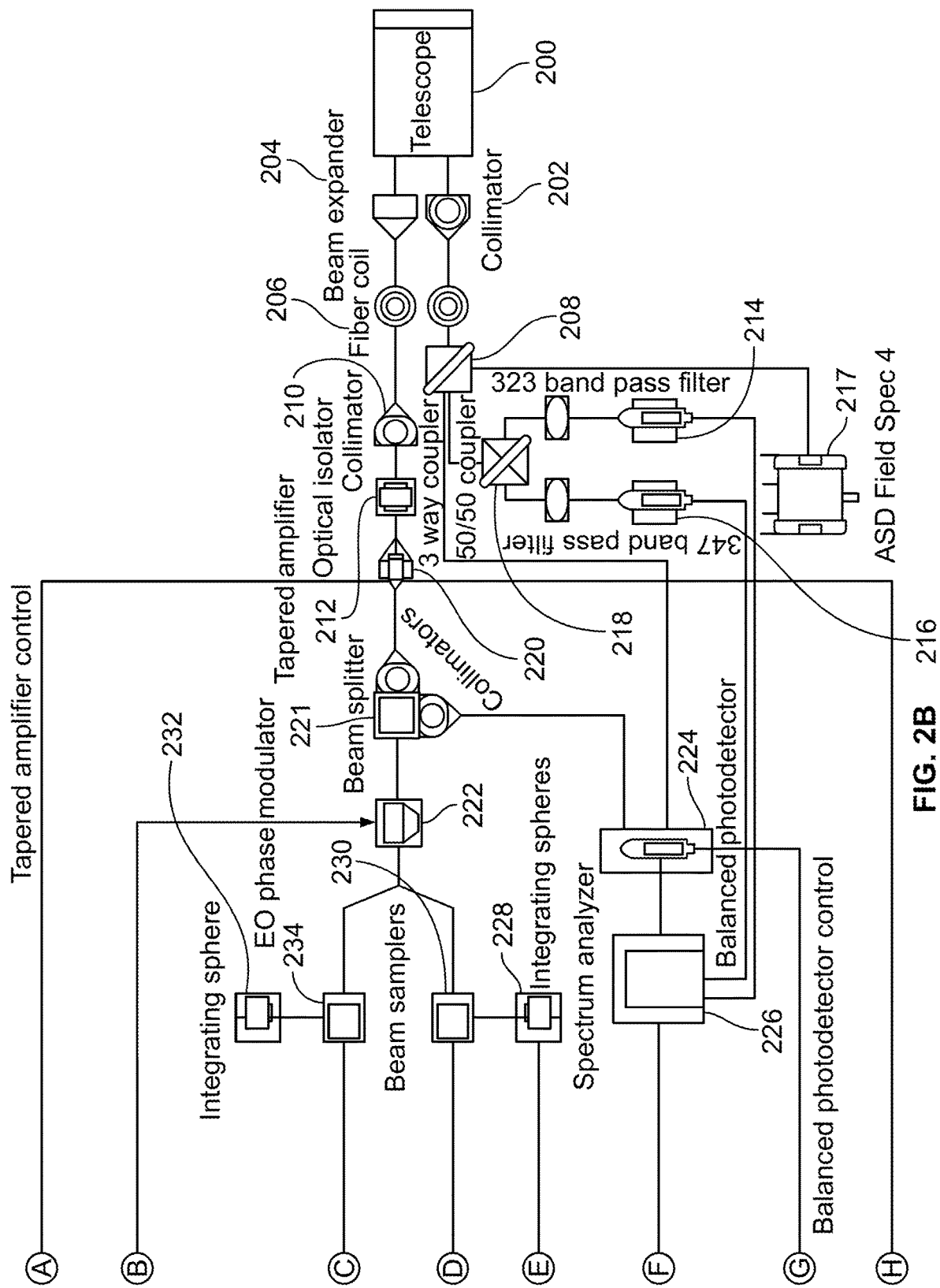

FIGS. 2A and 2B are schematics of the individual components of the SOTDiAL device of an embodiment of the present invention. This embodiment includes telescope 200, collimator 202, beam expander 206, three way coupler 208, collimator 210, optical isolator 212, 823 band pass filter 214, 847 band pass filter 216, ASD field spec 4 217, 50/50 coupler 218, tapered amplifier 220, beam splitter 221, EO phase modulator 222, balanced photodetector 224, spectrum analyzer 226, integrating sphere 228, beam samplers 230 and 234, integrating sphere 232, beam shutters 236 and 240, 823 nm laser 238, optical isolators 237 and 242, 847 nm laser 244, laser controllers 246 and 247, DAQ controller 250, and user interface 252 (processor).

Figure 3:
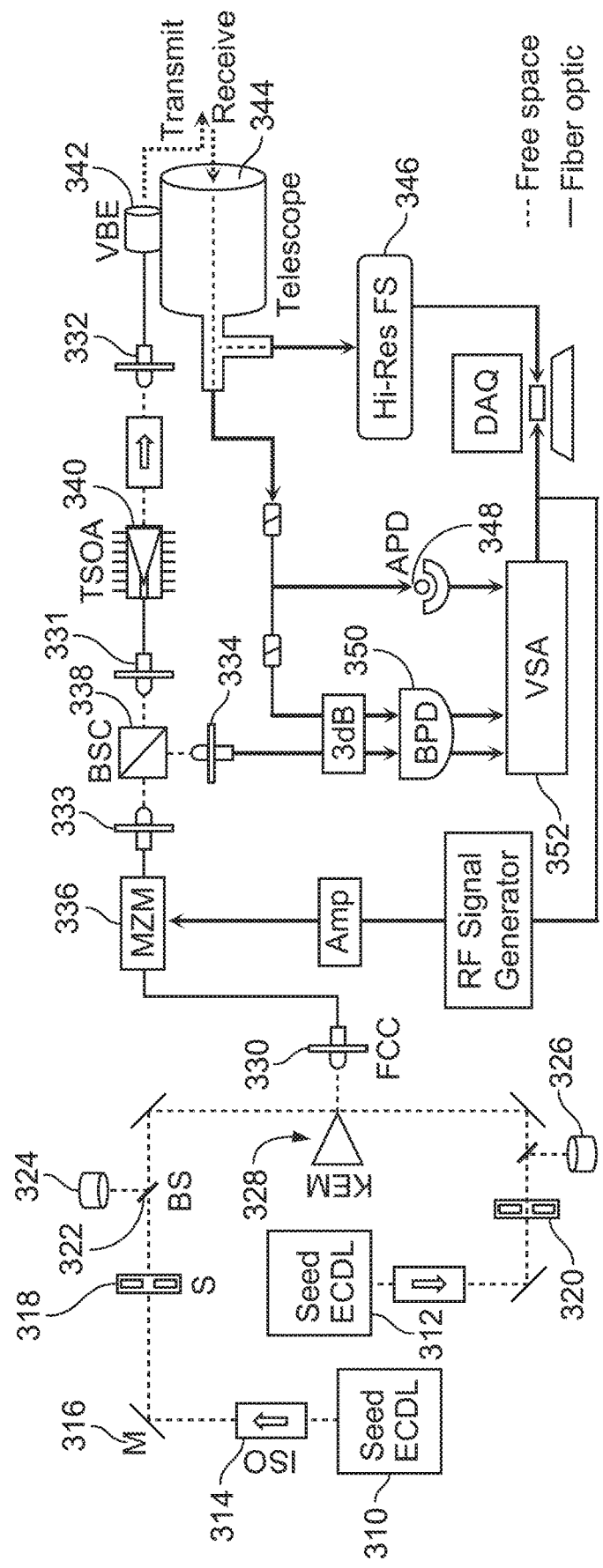
FIG. 3 is a schematic of the individual components of the SOTDiAL device of another embodiment of the present invention.

FIG. 3 is a schematic of the individual components of the SOTDiAL device of another embodiment of the present invention. This embodiment includes external cavity diode laser 310 and 312; optical isolator 314; dielectric mirror 316; shutters 318 and 320; beam sampler 322; integrating spheres 324 and 326; knife-edge mirror 328; fiberport collimation couplers 330-334; mach-zehnder-amplitude modulator 336; beamsplitter cube 338; tapered semiconductor optical amplifier 340; variable beam expander 342 adapted to transmit light; optical aperture 344 adapted to receive light; high-resolution field spectroradiometer 346; avalanche photodetector 348; balanced photodetector 350; and vector signal analyzer 352.

Figure 4:
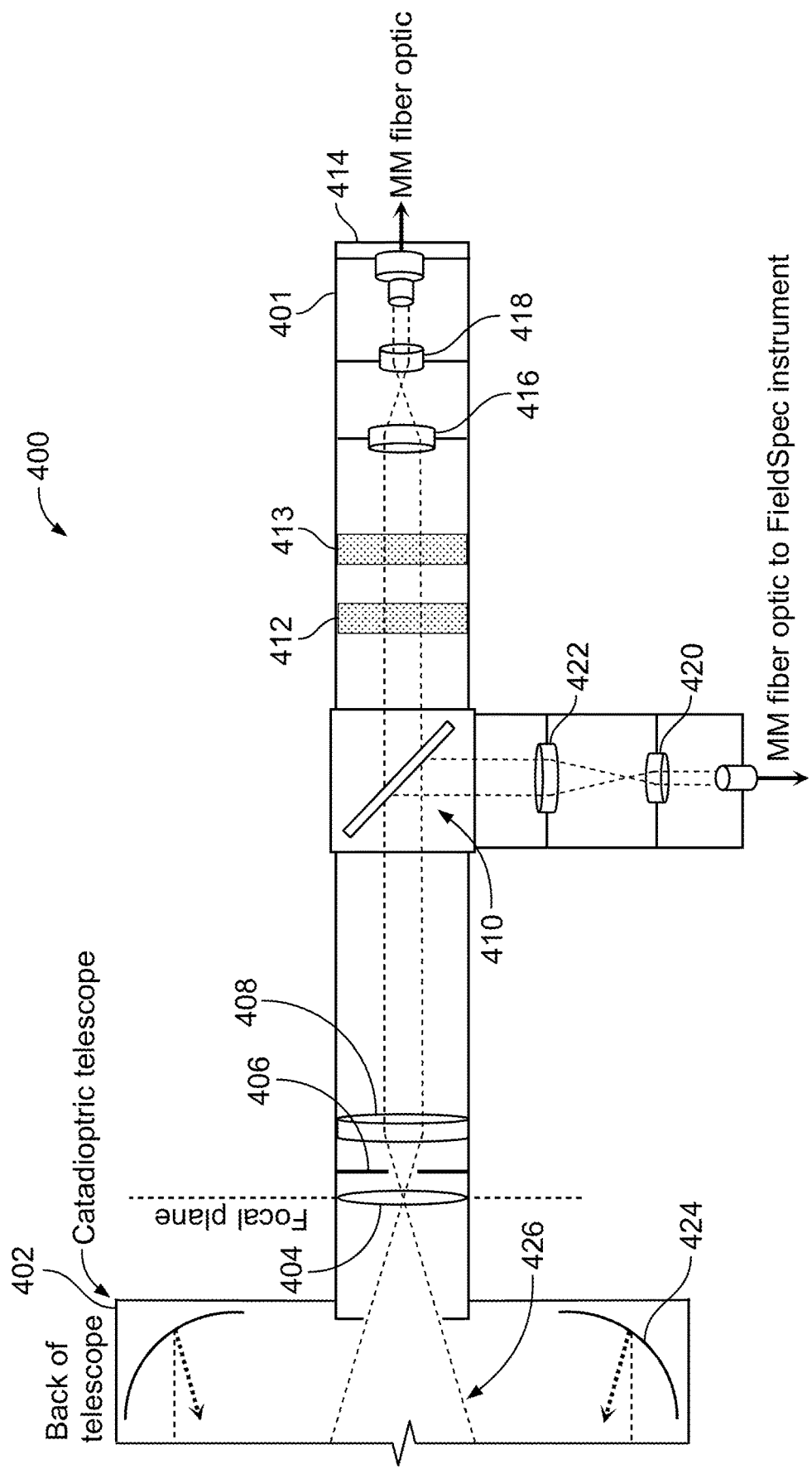
FIG. 4 illustrates a dual-channel optical receiver design for a SOTDiAL instrument of an embodiment of the present invention.

FIG. 4 illustrates a dual-channel optical receiver 400 which may be used with a SOTDiAL instrument of the present invention. Dual-channel optical receiver 400 includes housing 401 which may be affixed to back of a telescope 402 which may be catadioptric and have a field aperture, $\emptyset$=203.2 mm, f/10, f=2003 mm. Housing 401 may include uncoated N-BK7 biconvex lens 404, f=50 mm; manually adjustable iris diaphragm 406; uncoated N-BK7 spherical lens 408, f=50 mm; uncoated broad transmission, 50/50 polka-dot beamsplitter 410; narrow bandpass filters 412-413; NIR-coated fiberport 414, f=4.6 mm; NIR-coated achromatic doublets 416 and 418, f=25 mm, f=10 mm; and uncoated aspheric lenses 420 and 422, f=12 mm, f=8 mm. Also included are primary mirrors 424 and secondary mirrors 426.

In use, the active and passive elements of system 10 operate in tandem. Specifically, light energy, such as laser light, is emitted onto the surface of soil, while the light is also received simultaneously into the instrument through the optical aperture. The laser light is partially scattered into the atmosphere, but some light energy is reflected into the aperture of the system, while the sun provides the remaining backscatter of light into the system.

Through analysis of the spectra of transmitted and received light and correlation with relative humidity at the soil surface, calculations are made to determine in situ properties of the soil, including soil water potential (i.e. soil suction) and important index properties of the soil that are utilized in classification of the soil, including plasticity and fines content of the soil. See Garner, C. D., 2017, "Development of a Multiband Remote Sensing System for Determination of Unsaturated Soil Properties," Ph.D. dissertation, University of Arkansas, Fayetteville, A R and Salazar, S. E., 2017, "Development of a Multimode Instrument for Remote Measurements of Unsaturated Soil Properties," Ph.D. dissertation proposal, University of Arkansas, Fayetteville, Ark. Both of these references are incorporated herein by reference.

Figure 5:
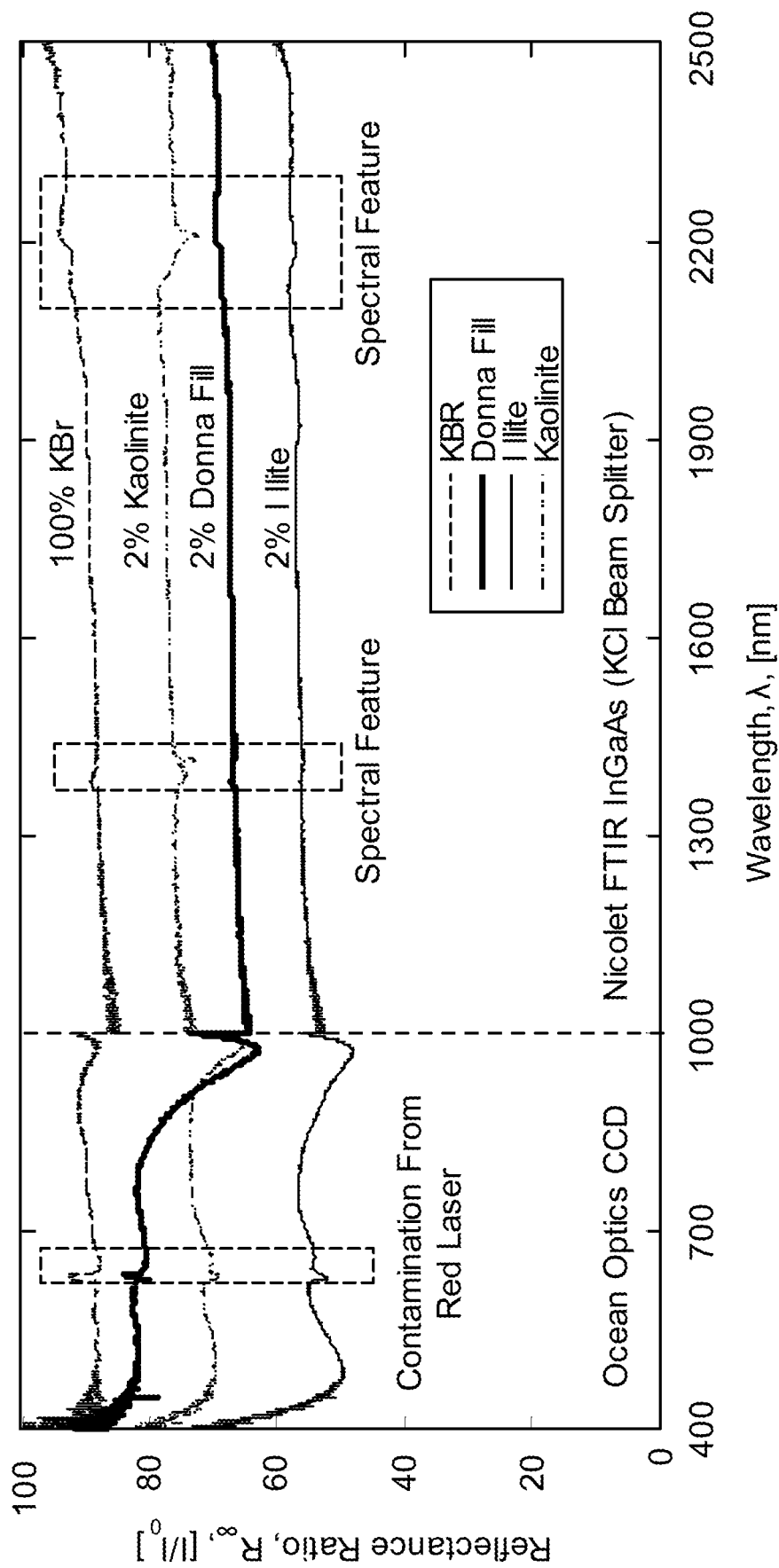
FIG. 5 shows a reflectance ratio for KBr substrate material (100 percent KBr) and two percent mass fractions samples of Donna fill, Illite, and Kaolinite (98 percent KBr: 2 percent soil) for of an embodiment of the present invention.

FIG. 5 shows a reflectance ratio for KBr substrate material (100 percent KBr) and two percent mass fractions samples of Donna fill, illite, and kaolinite (98 percent KBr: 2 percent soil) for of an embodiment of the present invention. This is an example of a part of the methodology, used for validation tests, as applied to three different soil mixture types (Donna Fill, illite, and kaolinite).

Figure 6:
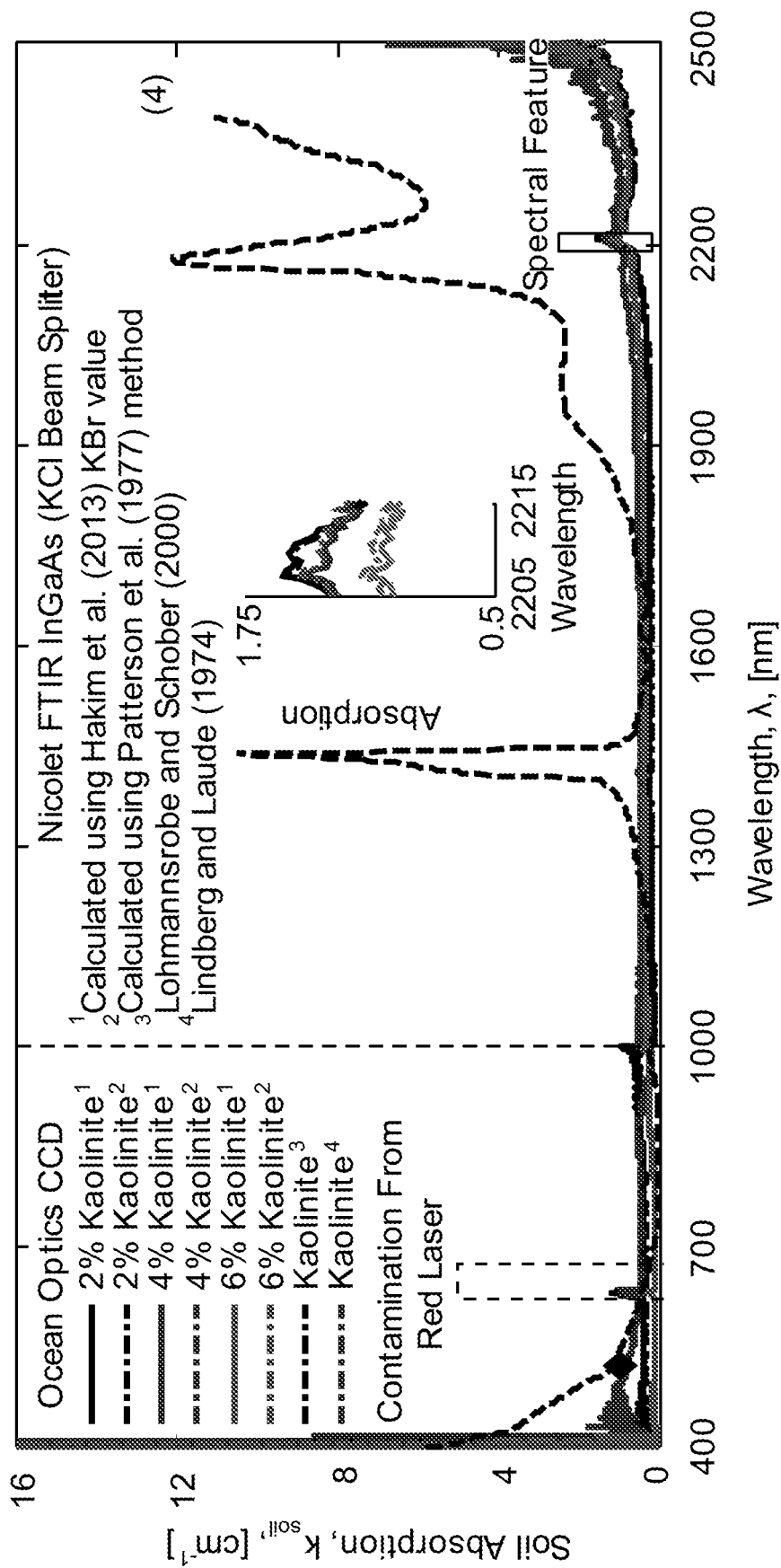
FIG. 6 shows a computed absorption coefficient for kaolinite material as determined using the procedure presented in Paterson et al. (1977) and as determined using KBr absorption values for of an embodiment of the present invention.

FIG. 6 shows a computed absorption coefficient for kaolinite material as determined using the procedure presented in Paterson et al. (1977) and as determined using KBr absorption values for of an embodiment of the present invention. This is an example of a part of the methodology, used for validation tests, as applied to kaolinite soil mixtures.

Figure 7:
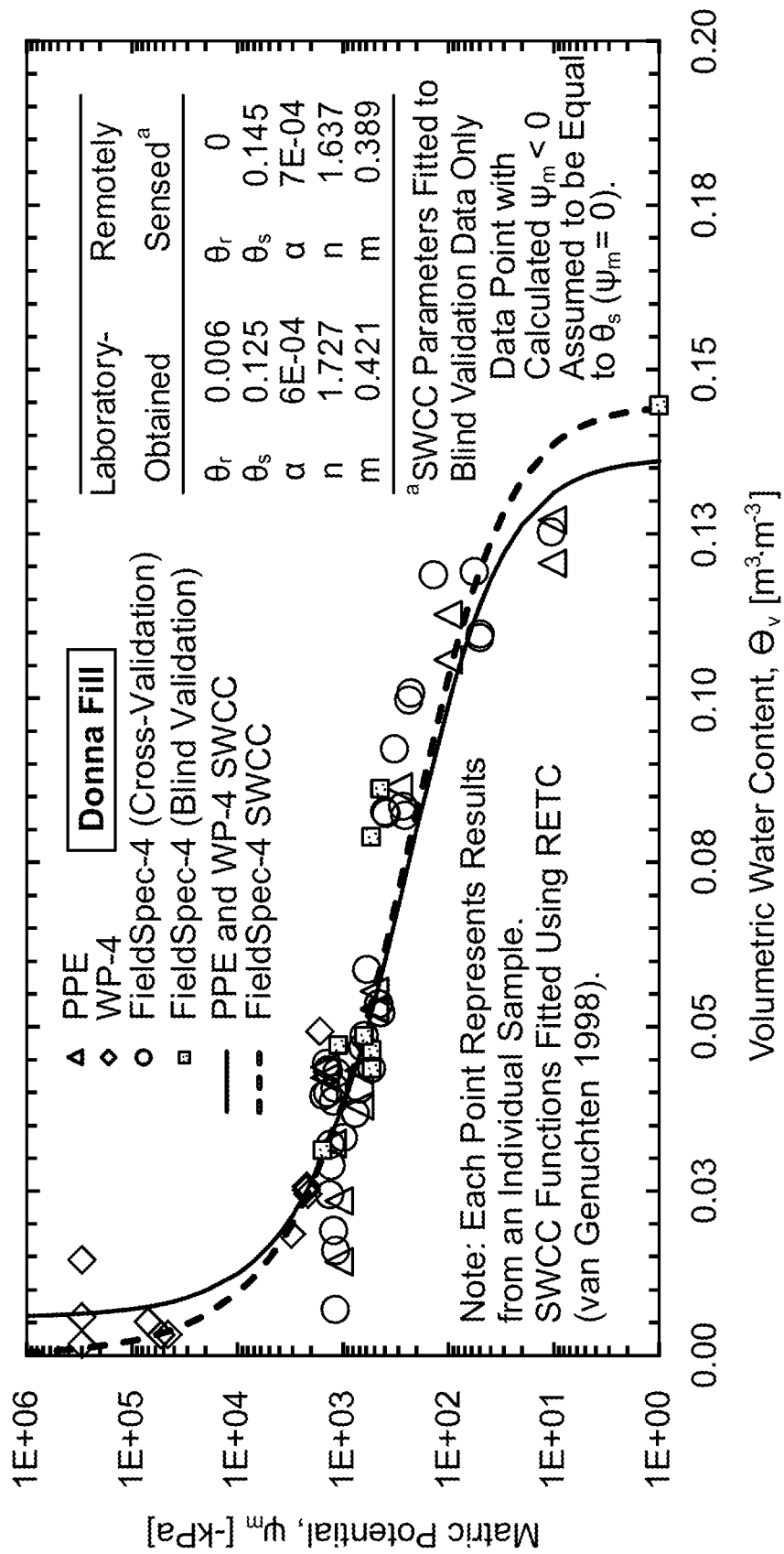
FIG. 7 shows WP-4, PPE, and FieldSpec-4 obtained measurements of the soil water characteristic curve, as developed for the Donna Fill Vis-NIR-Wet samples for of an embodiment of the present invention.

FIG. 7 shows WP-4, PPE, and FieldSpec-4 obtained measurements of the soil water characteristic curve, as developed for the Donna Fill Vis-NIR-Wet samples for of an embodiment of the present invention. This is an example of the application of the methodology to derive the soil water characteristic curve for Donna Fill soil. The results from this remotely-sensed methodology are compared to results obtained using traditional laboratory techniques.

Figure 8B:
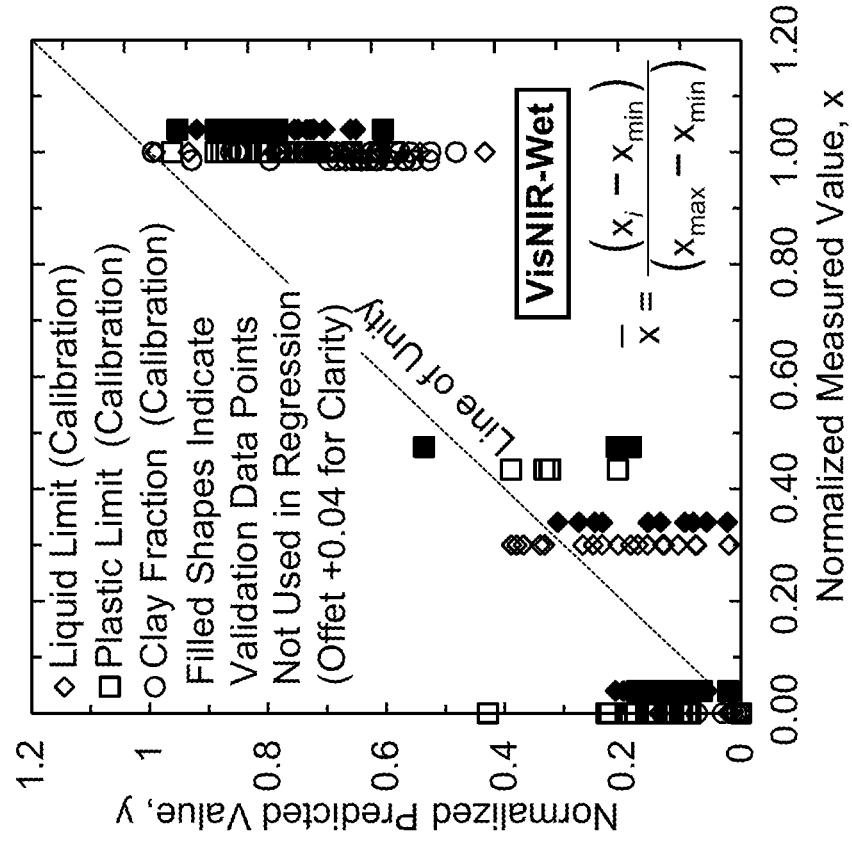
FIG. 8A shows normalized predicted values compared to the normalized measured values for the Vis-NIR-Dry spectra and 8B) normalized predicted values compared to the normalized measured values for the Vis-NIR-Wet spectra for of an embodiment of the present invention.
Figure 8A:
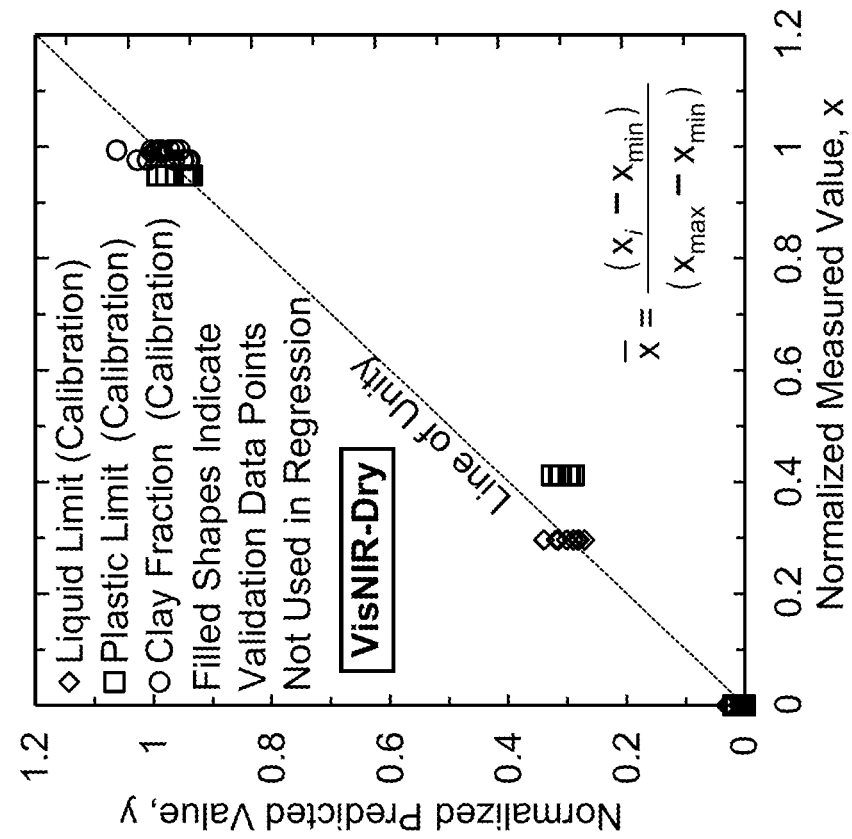

FIG. 8 shows normalized predicted values compared to the normalized measured values for the Vis-NIR-Dry spectra and b) normalized predicted values compared to the normalized measured values for the Vis-NIR-Wet spectra for of an embodiment of the present invention. This is an example of the statistical application of the methodology to derive the soil plasticity characteristics, used for validation tests.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiments, methods, and examples, but by all embodiments and methods within the scope and spirit of the disclosure.

The invention claimed is:

1. A soil analysis system comprising:
a light generating system; a light receiving system; and data processing system;
said light generating system comprising a first laser having a predetermined wavelength and a second laser having a predetermined wavelength that is different than the wavelength of said first laser;
said light receiving system comprising an aperture adapted to receive sunlight and backscattered laser light generated by said first laser and said second laser, said aperture in communication with a first and second beamsplitter, said first beamsplitter separating received sunlight from received backscattered laser light and said second beamsplitter further dividing received backscattered laser light;
a first photodetector connected to said first beamsplitter;
a second photodetector connected to said second beamsplitter;
a third photodetector connected to said second beamsplitter; and
said data processing system comprised of a spectrum analyzer adapted to receive and interpret signals from said first, second and third photodetectors.

2. The soil analysis system of claim 1 wherein said first laser has a near-infrared wavelength that is absorbed by the water in the soil and said second laser has a near-infrared wavelength that is absorbed at a lower level by the water in the soil.

3. The soil analysis system of claim 1 wherein said first laser has a wavelength of 823.20 nm and said second laser has a wavelength of 847.00 nm.

4. The soil analysis system of claim 1 further including an optical fiber that connects first beamsplitter to said first photodetector, said optical fiber transmits light received by said first beamsplitter to said first photodetector.

5. The soil analysis system of claim 4 further including a second optical fiber that connects second beamsplitter to said second and third photodetectors, said second optical fiber transmits light received by said second beamsplitter to said second and third photodetectors.

6. A soil analysis system comprising:
a plurality of lasers having different predetermined wavelengths;
an optical receiver having an aperture for receiving backscattered light including sunlight backscatter and laser backscatter; and
a plurality of beamsplitters, each of said beamsplitters direct backscattered light into a different channel, one of said channels including a pair of photodiode receivers adapted to receive said laser backscatter and another channel including a photodiode receiver adapted to receive sunlight backscatter.

7. The soil analysis system of claim 6 wherein one laser has a near-infrared wavelength that is absorbed by the water in the soil and another laser has a near-infrared wavelength that is absorbed at a lower level by the water in the soil.

8. The soil analysis system of claim 6 wherein one of said lasers has a wavelength of 823.20 nm and another of said lasers has a wavelength of 847.00 nm.

9. The soil analysis system of claim 6 further including one or more optical fibers that connect said beamsplitters to said photodiode receivers.

10. A method for analyzing soil comprising the steps of:
providing a light generating system; a light receiving system; and data processing system;
said light generating system comprising a first laser having a predetermined wavelength and a second laser having a predetermined wavelength that is different than the wavelength of said first laser;

emitting onto the surface of the soil light generated by said first and second lasers;

said light receiving system comprising an aperture in communication with a first beamsplitter and a second beamsplitter;

receiving backscattered sunlight;

receiving backscattered generated light emitted onto the surface of the soil by said first and second lasers;

said first beamsplitter separating received sunlight backscatter from received backscattered laser light and said second beamsplitter further dividing received backscattered laser light generated by said first laser and said second laser;

a first photodetector connected to said first beamsplitter;

a second photodetector connected to said second beamsplitter;

a third photodetector connected to said second beamsplitter;

said data processing system comprised of a spectrum analyzer adapted to receive and interpret signals from said first, second, and third photodetectors; and analyzing the spectra of emitted and received light to form a correlation with relative humidity at the soil surface to determine an in situ property of the soil.

11. The method of claim 10 wherein said in situ property is soil water potential.

12. The method of claim 10 wherein said in situ property is soil plasticity.

13. The method of claim 10 wherein said in situ property is the fines content of the soil.

14. The method of claim 10 wherein said first laser has a near-infrared wavelength that is absorbed by the water in the soil and said second laser has a near-infrared wavelength that is absorbed at a lower level by the water in the soil.

15. The method of claim 10 wherein said first laser has a wavelength of 823.20 nm and said second laser has a wavelength of 847.00 nm.

16. The method of claim 10 further including an optical fiber that connects said first beamsplitter to said first photodetector, said optical fiber transmits light received by said first beamsplitter to said first photodetector.

17. The method of claim 16 further including a second optical fiber that connects second beamsplitter to said second and third photodetectors, said second optical fiber transmits light received by said second beamsplitter to said second and third photodetectors.

18. The method of claim 10 wherein said spectra of emitted and received light is obtained from a 360-degree sampling of the soil.

19. The method of claim 10 wherein said spectra of emitted and received light is obtained from a 360-degree sampling of the soil and a range up to 1500 feet.

20. The method of claim 10 wherein light is emitted and received simultaneously.

* * * * *